US008731716B2

(12) United States Patent
Jacobsen et al.

(10) Patent No.: US 8,731,716 B2
(45) Date of Patent: May 20, 2014

(54) CONTROL LOGIC FOR BIOMIMETIC JOINT ACTUATORS

(75) Inventors: Stephen C. Jacobsen, Salt Lake City, UT (US); Marc X. Olivier, Sandy, UT (US); Brian J. Maclean, Salt Lake City, UT (US)

(73) Assignee: Raytheon Company, Waltham, MA (US)

( * ) Notice: Subject to any disclaimer, the term of this patent is extended or adjusted under 35 U.S.C. 154(b) by 645 days.

(21) Appl. No.: 13/061,488

(22) PCT Filed: Aug. 28, 2009

(86) PCT No.: PCT/US2009/055423
§ 371 (c)(1),
(2), (4) Date: Aug. 17, 2011

(87) PCT Pub. No.: WO2010/025403
PCT Pub. Date: Mar. 4, 2010

(65) Prior Publication Data
US 2011/0295164 A1    Dec. 1, 2011

Related U.S. Application Data

(60) Provisional application No. 61/092,692, filed on Aug. 28, 2008.

(51) Int. Cl.
*G06F 19/00* (2011.01)
*G05B 19/04* (2006.01)

(52) U.S. Cl.
USPC ............ 700/245; 700/248; 700/250; 700/251

(58) Field of Classification Search
USPC .................................. 700/245, 248, 250, 252
See application file for complete search history.

(56) References Cited

U.S. PATENT DOCUMENTS

| 4,955,918 A | 9/1990 | Lee |
| 5,092,646 A | 3/1992 | Smallridge |

(Continued)

FOREIGN PATENT DOCUMENTS

| EP | 1535705 | 6/2005 |
| JP | S61-184264 | 8/1986 |

(Continued)

OTHER PUBLICATIONS

U.S. Appl. No. 13/061,482, filed May 24, 2011; Stephen C. Jacobsen; notice of allowance dated Apr. 19, 2013.

(Continued)

*Primary Examiner* — Ian Jen
(74) *Attorney, Agent, or Firm* — Thorpe North & Western LLP

(57) ABSTRACT

A method of operating a biomimetic mechanical joint having a plurality of fractional actuators configured for rotating a support member about a pivot device. The fractional actuators can be selectively recruited during operation, either individually or together, to efficiently rotate the support member about the mechanical joint throughout a range of movements and under a variety of load conditions. Each fractional actuator can be continuously throttled to reduce the speed or torque at which the actuator operates. The capability of selectively recruiting and throttling each fractional actuator results in an actuator system having two degrees of freedom, in which a single operating state of the mechanical joint may be reached with one or more of actuator arrangements and throttling settings. The method of the present invention allows for selection from the available actuator arrangements and throttle settings according to predetermined operating modes such as high-efficiency, high-acceleration or general-purpose, etc.

20 Claims, 7 Drawing Sheets

(56) References Cited

U.S. PATENT DOCUMENTS

| | | |
|---|---|---|
| 5,207,114 A | 5/1993 | Salisbury et al. |
| 5,282,460 A | 2/1994 | Boldt |
| 5,502,363 A | 3/1996 | Tasch et al. |
| 5,549,712 A | 8/1996 | Gammer et al. |
| 5,873,734 A | 2/1999 | Griswold et al. |
| 5,888,235 A | 3/1999 | Jacobsen et al. |
| 6,966,882 B2 | 11/2005 | Horst |
| 7,066,896 B1 | 6/2006 | Kiselik |
| 7,087,031 B2 | 8/2006 | Rossi et al. |
| 7,308,848 B2 | 12/2007 | Jacobsen |
| 7,628,766 B1 | 12/2009 | Kazerooni et al. |
| 7,935,153 B2 | 5/2011 | Auberger |
| 8,052,185 B2 | 11/2011 | Madhani |
| 8,231,687 B2 | 7/2012 | Bedard et al. |
| 2003/0030397 A1 | 2/2003 | Simmons |
| 2004/0128028 A1 | 7/2004 | Miyamoto et al. |
| 2004/0158175 A1 | 8/2004 | Ikeuchi et al. |
| 2004/0172165 A1 | 9/2004 | Iribe et al. |
| 2004/0176875 A1 | 9/2004 | Iribe et al. |
| 2007/0162152 A1 | 7/2007 | Herr et al. |
| 2007/0162404 A1 | 7/2007 | Gorelik et al. |
| 2009/0210093 A1 | 8/2009 | Jacobsen |

FOREIGN PATENT DOCUMENTS

| | | |
|---|---|---|
| JP | S6384888 | 4/1988 |
| JP | 03-234495 | 1/1991 |
| JP | 2001287177 | 10/2001 |
| WO | WO 98/30177 | 7/1998 |
| WO | WO 2010/025409 | 3/2010 |

OTHER PUBLICATIONS

U.S. Appl. No. 13/061,482, filed May 24, 2011; Stephen C. Jacobsen.

U.S. Appl. No. 13/061,472, filed May 23, 2011; Stephen C. Jacobsen.

PCT Application PCT/US2009/055440; filed Aug. 28, 2009; Stephen C. Jacobsen; International Search Report mailed Jan. 14, 2011.

PCT Application PCT/US2009/055423; filed Aug. 28, 2009; Stephen C. Jacobsen; International Search Report mailed Dec. 22, 2009.

PCT Application PCT/US2009/055429; filed Aug. 28, 2009; Stephen C. Jacobsen; International Search Report mailed Jan. 8, 2010.

CONTROL LOGIC FOR BIOMIMETIC JOINT ACTUATORS

RELATED APPLICATIONS

This application claims priority to U.S. Provisional Patent Application No. 61/092,692, filed Aug. 28, 2008, and entitled "Control Logic for Biomimetic Joint Actuators," which application is incorporated by reference in its entirety herein.

This invention was made with government support under W911NF-05-0111 awarded by the U.S. Army. The government has certain rights in the invention.

FIELD OF THE INVENTION

The field of the invention relates generally to human-like robotic devices, and more specifically to the mechanical joints for powered prosthetic limbs, exoskeletons and human-like robots.

BACKGROUND OF THE INVENTION AND RELATED ART

Significant advancements in the development of robots and robotic devices have been achieved in recent decades. Manufacturing efficiencies gained through the use of robotic assemblers and manipulators, exploratory robotic vehicles (such as those traveling the surface of Mars), and animatronics characters often seen at theme parks and other sights of attraction are but a few popular examples. Each of these specialized robots have common characteristics, however, in that they do not have true human-like capabilities, nor do they function with human-like operation. Indeed, many robotic devices are tethered to external power sources, while others are configured to move without bi-pedal or human-like locomotion. True mobile and un-tethered human-like robots and exoskeletons, while in existence, are in the early stages of development, and are continually being improved to better participate in mobile, human-like activities.

One reason for the continuing technological difficulty in advancement of human-like, or biomimetic, robotic systems toward un-tethered human-like robotic activity is the inefficiency inherent within the mechanical joints that provide the robots with the ability to move. In a robotic device, movement about a mechanical joint is a primary consumer of power. Yet with few exceptions the mechanical joints in robots and human assistance devices have been optimized for control and performance, these taking precedence over optimal efficiency considerations. For instance, many modern non-biomimetic industrial robots perform significant work with the advantage of being permanently connected to external electrical, fluid or mechanical power systems that can supply a surplus of power, leading to articulating joints capable of precise and powerful movements, but which are also highly wasteful of energy.

Efficiency has also suffered in powered prosthetic limbs as these devices have been primarily confined to the laboratory, research centers, or individuals living in populated areas with ready access to sources of power. In a remote work or battlefield environment, however, efficiency is critical for long-term operation and/or survivability, as an exoskeleton or human-like robot is useless if it prematurely runs out of fuel or discharges its batteries. Advancements in more efficient operation of human-like robotic devices or exoskeletons, particularly more efficient operation of the biomimetic joints through a range of movements and load conditions, without sacrificing speed or power, are greatly needed and will serve to provide improved, un-tethered human-like robotic activity.

SUMMARY OF THE INVENTION

The human body can be one model for optimizing the mechanical joints in exoskeletons and humanoid robots for efficiency. The bodies of all species in the animal kingdom, including humans, have been selected over time for highly-efficient operation, in order to function and survive with only a last meal or stored fat for energy. The ability to emulate the efficient movement of a human limb around a natural joint can be provided, at least in part, with a biomimetic system, and more particularly with a biomimetic mechanical joint within the biomimetic system.

In the present invention, this includes providing a biomimetic mechanical joint with the ability to move a limb segment or support member about a pivot device using a plurality of fractional actuators, similar to the way a plurality of individual muscles and muscles groups in the human body are configured to efficiently rotate a natural joint. The fractional actuators can be selectively recruited during operation, either individually or together, using a calculated switching or recruiting logic to efficiently rotate the support member about the mechanical joint throughout a range of movements and under a variety of load conditions. Each fractional actuator can also be continuously throttled to reduce the speed or torque at which the actuator operates. The ability to selectively recruit and throttle each fractional actuator results in an actuator system having two degrees of freedom, in which a single operating state of the mechanical joint may be reached with one or more actuator recruitment arrangements and throttling settings.

In accordance with the invention as embodied and broadly described herein, the present invention resides in a method for operating a biomimetic mechanical joint, and more particularly for providing a control logic platform for operating the biomimetic mechanical joint, including the step of obtaining a biomimetic mechanical joint having a first and second fractional actuators that are configured for rotating a support member about a pivot device. According to the control logic, the first and second fractional actuators can each be selectively recruited for or disengaged from driving the mechanical joint, and can be continuously throttled when driving the mechanical joint. The method or the control logic can also include the steps of operating the first and second fractional actuators to rotate the support member about the pivot device, monitoring a user input for the mechanical joint, measuring the actual, or first, operating state of the mechanical joint, and calculating an error function between the user input and the first operating state. The method or control logic can further include using the error function to identify one or more powering configurations for the first and second fractional actuators that is capable of reducing the error function, selecting from the identified powering configurations, and causing the mechanical joint to enter a second operating state based on the selected powering configuration.

BRIEF DESCRIPTION OF THE DRAWINGS

Features and advantages of the invention will be apparent from the detailed description that follows, and which taken in conjunction with the accompanying drawings, together illustrate features of the invention. It is understood that these drawings merely depict exemplary embodiments of the present invention and are not, therefore, to be considered limiting of its scope. And furthermore, it will be readily appreciated that the components of the present invention, as generally described and illustrated in the figures herein, could be arranged and designed in a wide variety of different configurations. Nonetheless, the invention will be described and explained with additional specificity and detail through the use of the accompanying drawings, in which.

DETAILED DESCRIPTION OF EXEMPLARY EMBODIMENTS

Figure 1:
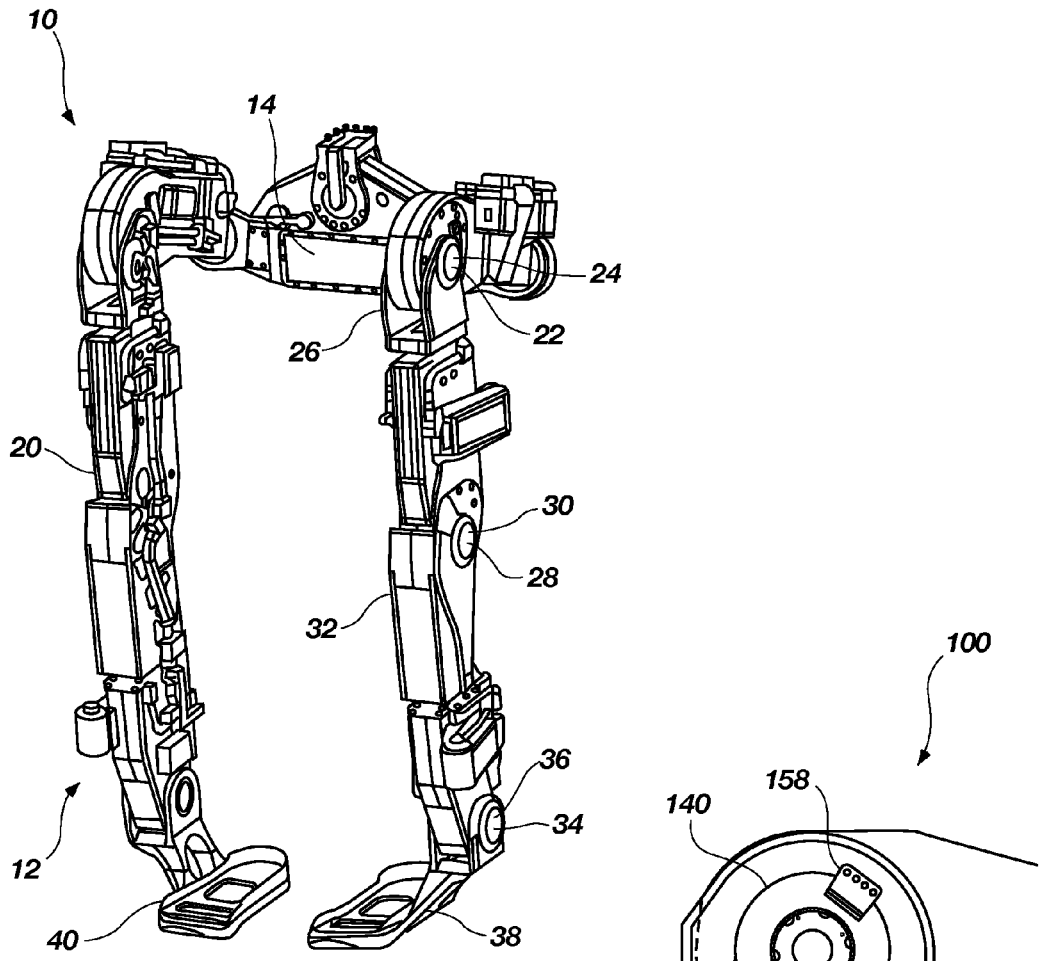
FIG. 1 illustrates a perspective view of an exemplary biomimetic system in the form of an exoskeleton which can provide a platform for the biomimetic mechanical joint operated in accordance with the method of the present invention.

The following detailed description of the invention makes reference to the accompanying drawings, which form a part thereof and in which are shown, by way of illustration, exemplary embodiments in which the invention may be practiced. While these exemplary embodiments are described in sufficient detail to enable those skilled in the art to practice the invention, it should be understood that other embodiments may be realized and that various changes to the invention may be made without departing from the spirit and scope of the present invention. As such, the following more detailed description of the exemplary embodiments of the present invention is not intended to limit the scope of the invention as it is claimed, but is presented for purposes of illustration only: to describe the features and characteristics of the present invention, and to sufficiently enable one skilled in the art to practice the invention. Accordingly, the scope of the present invention is to be defined solely by the appended claims.

Illustrated in FIGS. 1-12 are various exemplary embodiments and applications of a method for operating a biomimetic mechanical joint within a biomimetic system, wherein the biomimetic joint comprises a plurality of fractional actuators, and wherein each of the fractional actuators is configured for rotating a support member of the joint about a pivot device. Such biomimetic mechanical joints can be integrated within powered prosthetic limbs, human-like robots, exoskeletons or other human-like robotic devices, etc. The method of the present invention can provide for operating the mechanical joint in accordance with a range of selectable 'modes' or operating strategies including, but not limited to, a high-efficiency mode based on minimum power usage, a high-acceleration mode based on maximum available power, and a general-purpose mode configured for operation between the high-efficiency and high-acceleration set points.

As stated above, the method of the present invention can be applied to biomimetic mechanical joints which use a plurality of fractional actuators. The fractional actuators can provide, either individually or in combination, for the motion requirements of the mechanical joint about a single degree-of-freedom ("DOF") axis. The biomimetic mechanical joint can be distinguished from prior art mechanical joints which use a single 100% actuator system to generate movement about the same axis. The use of multiple fractional actuators, instead of one 100% actuator, can lead to significant improvements in both efficiency and performance.

A 'fractional' actuator can be defined as an actuator that meets less-than-100% of the maximum design torque of the mechanical joint, which is the standard design point for most actuation systems. In some exemplary embodiments of the present invention biomimetic mechanical joints, a first fractional actuator can be combined with at least one other fractional actuator so that the set of fractional actuators, operating together, meets the maximum design torque requirement of the mechanical joint. While the number of fractional actuators can be three or more, it is to be appreciated that an actuation system with just two fractional actuators can provide significant improvements over the prior art which uses a single, 100% actuator to meet the maximum design torque requirement.

The fractional split between a two fractional antagonistic actuator system can range anywhere from 95/5 to 50/50, and can further vary among the locations of the biomimetic mechanical joints throughout the human-like robotic body. The optimum ratio will depend upon the performance boundary conditions of the mechanical joint, and will vary considerably upon the designated purpose of the robotic body (e.g. general purpose, heavy lifting, running, climbing assist, etc.) and the type and configuration of the actuators in the actuator system. However, a biomimetic mechanical joint with two fractional antagonistic actuators configured for optimal efficiency can have a fractional split generally ranging between 80/20 and 60/40.

As previously described, the biomimetic mechanical joint can comprise a set of multiple fractional actuators which operate to rotate a limb segment or support member about a pivot device, and can be applied to any major load-bearing joint in a human-like robotic body, including but not limited to, the hip, knee, ankle, shoulder, elbow, wrist, etc. Each biomimetic mechanical joint can be further defined as the assembly which includes both the pivot device, the actuators, and the attached, movable support member. For instance, a biomimetic hip can include the hip joint and the upper leg support member. In a similar fashion, a biomimetic knee can include both the knee joint and the lower leg, and the biomimetic ankle can include the ankle joint and the foot, etc.

An exemplary biomimetic mechanical joint for generating a variable torque between support members of a biomimetic robotic device is described in more detail in commonly-owned and co-pending Patent Application No. PCT/US09/

55429, filed Aug. 28, 2009, and entitled "Biomimetic Mechanical Joint,", which application is incorporated by reference in its entirety herein.

The present invention can provide several significant advantages over prior-related mechanical joints, some of which are recited here and throughout the following more detailed description. First, the biomimetic mechanical joint can be significantly more efficient than the mechanical joints in existing prosthetic limbs, exoskeletons, human-like robots or robotic devices using a single, 100% actuator system. One reason for the improved efficiency is that fractional actuators creating motion about each DOF axis better emulate the structure of the human body, which naturally uses only just enough muscle to meet the performance required of the joint or limb at any particular time. In other words, energy is conserved in a human joint by selectively recruiting, or activating, only the individual muscles or muscle groups needed to move the attached support member or support member in the desired manner.

Single, 100% actuator systems have a disadvantage in that all of the actuator must be activated all of the time. Unless the actuator is operating at its optimum design point, it is wasting energy. For example, in a hydraulic system using a hydraulic cylinder sized to the maximum torque requirement, the wasted energy can be embodied in the excess high-pressure hydraulic fluid that is used to move the hydraulic piston under little or no load. Moreover, as the motion of the actuator may be excessively fast even when there is a load to press against, the high-pressure fluid is often throttled by the pressure control valve so that the support member moves at a slower, more desirable pace. Both the use of excess fluid and the throttling are examples of wasting the potential energy contained in the pressurized hydraulic fluid.

The biomimetic mechanical joint overcomes the inherent disadvantages of the prior art by splitting the single actuator per DOF into two or more fractional actuators per DOF. In essence, using a plurality of fractional actuators creates a gear shifting scenario in which the one or more actuators can be selectively recruited to efficiently meet all the operating scenarios that may be required of the joint. Thus, at any particular operating condition which is less than the maximum design torque condition for the joint, one or the other or both of the fractional actuators can be operating near its optimum and most efficient design point.

It can be appreciated by one of skill in the art that configuring the plurality of fractional actuators to function effectively throughout the entire operating range requires that the actuators be first sized to meet the extreme conditions defining the limits of that range. It can also be recognized that the two boundary conditions defining the limits of that range comprise the maximum design torque at zero speed (also known as the low-speed/high-torque boundary condition), and the maximum rotational speed of the mechanical joint under zero additional load (also known as the high-speed/low-torque boundary condition).

To meet these two boundary conditions, the first fractional actuator can be configured to meet the demands of a high-speed, quick-response operating state, such as when a leg must move quickly to catch the body during a stumble and to recover balance without falling (e.g. stumble-recovery). This operating state is consistent with the high-speed/low-torque boundary condition at one end of the operating range. Furthermore, both the first and a second fractional actuators can be sized so that together they meet the other boundary condition, which is the low-speed/high-torque response state. In doing so, the second fractional actuator can be individually sized by subtracting the contribution of the first fractional actuator from the low-speed/high-torque boundary condition.

The efficiency of the biomimetic mechanical joint can be improved without sacrificing performance by separating the single actuator into two or more actuators, which are then sized for rated operation that meets the two boundary conditions relating to maximum speed and maximum torque. Rated operation can be defined as operation at 100% of design limit, whether those design limits are generated torque, acceleration, speed of motion, flow rates, etc. Most actuators can operate at levels substantially less than 100% of design ratings, such as with throttling of the pressurized hydraulic fluid as it passes through the pressure valve, or reducing the voltage to a motor drive, etc. Such throttling or reduction in voltage at non-100% design levels is inefficient. It is the purpose of one embodiment of the present invention to operate the fractional actuators driving the biomimetic mechanical joint at or near rated power during all operating states, as this is the most efficient operating point.

This operating strategy is analogous to the geared transmission system in a motorized vehicle, which allows the engine to operate at its most efficient or most powerful operating points even while the vehicle is moving at highly different speeds. For instance, a vehicle transmission system typically has three or more gears that split the operating range of the vehicle into three or more operating regions, ranging from low speed, high torque (starting from rest) to high-speed, low-torque (overdrive on the freeway). With the geared transmission system, the engine can power the vehicle near its optimum efficiency or power points as the vehicle moves through all operating regions, which the engine could not do if it were directly connected to the wheels.

In a similar fashion, the fractional actuators of a biomimetic mechanical joint can be configured to operate together or individually to create three or more operating regions. In a biomimetic joint utilizing two fractional actuators, one actuator can be larger than the other. Both fractional actuators can be sized (or torque rated) together for the low-speed/high-torque operating region. The smaller fractional actuator also can be individually sized (or speed rated) for optimal performance in the high-speed/low-torque operating region. Therefore, the larger fractional actuator can individually function as the middle gear, to fill the gap between the combined high-torque operation and smaller actuator's high-speed operation. Furthermore, each fractional actuator may still be continuously throttled to meet non-rated operating conditions. As will be seen, however, the degree of throttling can be greatly reduced across the operating range of the plurality of fractional actuators in comparison to an actuation system built with single, 100% actuator.

It can be appreciated that there is little room for a gear system within the support member, which would allow the first, second, third or higher gears to be selectively inserted and removed from the power transmission path. Moreover, even if there were space available, there may not be enough time to switch gears as the actuators may require near-instantaneous activation during a single movement of the mechanical limb or support segment. Thus, it can be desirable for each fractional actuator of a biomimetic mechanical joint to have its own coupling path to the pivot device. When one or the other fractional actuators is individually recruited to power the biomimetic mechanical joint, however, there can be a means for selectively disengaging or disconnecting the non-recruited actuator from the power path, so that while the inactive actuator is not contributing to the forces driving the joint, it is not creating excess drag on the system either. This selective disengagement can include a fluidic (e.g. hydraulic or pneumatic) disengagement between the actuators and a fluid supply, an electrical disconnection between a linear or rotary motor and a power supply, or a physical disconnection between the antagonistic actuators and a drive pulley, etc.

As stated above, the fractional actuators can be selectively recruited during operation, either individually or together, to efficiently rotate the support member about the mechanical joint throughout a range of movements and under a variety of load conditions. As also pointed out, each fractional actuator can be continuously throttled to reduce the speed or torque at which the joint operates. The ability to selectively recruit and throttle each fractional actuator results in an actuator system having two degrees of freedom, in which a single operating state of the mechanical joint may be reached with one or more of actuator recruitment arrangements and throttling settings, also known as a powering configuration. The method of the present invention can provide for the continuous identification and selection of the powering configuration that best meets the desired mode of operation, e.g. high-efficiency, high-acceleration, general purpose, etc.

It is to be appreciated that the method of the present invention can be applied to biomimetic mechanical joints with various types of fractional actuators. For instance, the fractional actuators can include fluidic power systems (e.g. hydraulics or pneumatics, etc.) or electrical power systems (e.g. linear or rotary motors, etc.). The method can also be applied to mechanical joints with fractional actuators assembled into a variety of configurations, such as single-acting linear antagonistic actuator pairs that rotate the pivot device with a pulley and tendon system, double-acting linear actuators attached to the pivot device with a rigid linkage, or rotary actuators integrated into the pivot device, etc.

Each of the above-recited advantages will be apparent in light of the detailed description set forth below and best understood with reference to the accompanying drawings, wherein the elements and features of the invention are designated by numerals throughout. These advantages are not meant to be limiting in any way. Indeed, one skilled in the art will appreciate that other advantages may be realized, other than those specifically recited herein, upon practicing the present invention.

Illustrated in FIG. 1 is an exemplary example of an exoskeleton 10, which can provide a platform for the various biomimetic mechanical joints operated in accordance with the method of the present invention. The exoskeleton has the potential to provide mechanical assistance to humans in variety of situations, including increased mobility for the handicapped, augmented physical labor, and enhanced soldiering activities. As shown, the exoskeleton can include a whole-body support frame. In another embodiment it can also include a partial body frame, such as the lower body walking portion, or even can be embodied in individual limbs. The biomimetic mechanical joint can be applied to any load-carrying support member on the exoskeleton, and is especially suitable for one or more joints in the legs or lower half of the body.

As shown in FIG. 1, the exoskeleton 10 can include a lower body portion 12. The lower body portion can include a pelvic region 14 to which are attached the two legs 20, each of which can be further comprised of a hip joint 22, a knee joint 28 and an ankle joint 34. For the purposes of this application, the biomimetic mechanical joint can be defined as the assembly which includes the pivot device, the attached rotary support member and the actuator sub-assembly. The actuator sub-assembly can often be mounted inside the rotary support member. The biomimetic mechanical hip joint 22 can therefore comprise the hip pivot device 24 and the upper leg or thigh support member 26, the knee joint 28 can comprise the knee pivot device 30 and the lower leg or calf support member 32, and the ankle joint 34 can comprise the ankle pivot device 36 and the foot support member 38. Load cells 40 can be located in each of the foot support members 38 or at other locations supported about the exoskeleton, and can be used to continuously monitor the user's motions or command inputs to generate command torques for the various mechanical joints.

Figure 2:
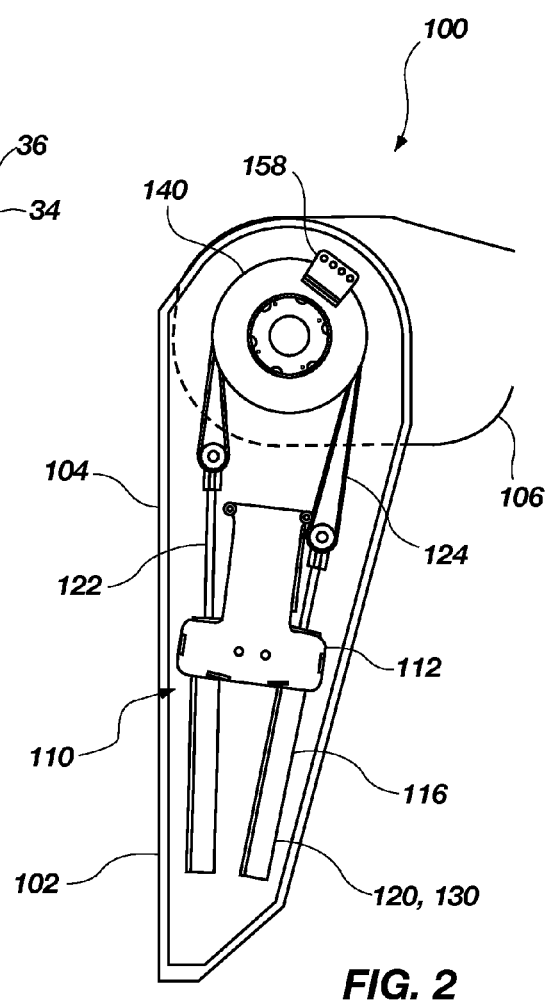
FIG. 2 illustrates a side view of an exemplary biomimetic mechanical joint having fractional actuators and operated in accordance with an exemplary embodiment of the present invention.

Illustrated in FIG. 2 is a side view of one exemplary biomimetic mechanical joint 100 that could be applied to any of the load bearing joints of the exoskeleton or human-like robotic device, and which can be operated in accordance with the method of the present invention. The biomimetic mechanical joint 100 can have a rigid outer shell 104 surrounding the pivot device 140 and forming the rotary support member 102 of the mechanical joint. Two fractional actuators 116, in this case two single-acting antagonistic actuator pairs 120, 130 can be included in an actuator sub-assembly 110 that is driven by a control system mounted within a control body 112 located between the antagonistic actuator pairs. Tendons 124 can be coupled at both ends to the actuator pistons 122 extending from the antagonistic actuator pairs 120, and at a midsection to a tendon attachment block 158 mounted to the pivot device. Alternatively, the single tendon can be subdivided into two tendons, with one end of each tendon coupled to a tendon attachment point on the pivot device and the other end of each tendon coupled to one of the actuators in the antagonistic actuator pair.

In the biomimetic mechanical joint 100 shown in FIG. 2, the actuator sub-assembly 110 can be mounted to the inside of the rigid shell 104 of the rotary support member 102, while the pivot device 140 can be fixed relative to a base support member 106. By way of an illustrative example, if the biomimetic mechanical joint were integrated in the hip joint of the exoskeleton of FIG. 1, the joint's actuator sub-assembly could be mounted to the inside of the upper leg or thigh support member while the hip pivot device was fixed relative to the pelvic region. In an alternative aspect of the biomimetic mechanical joint, however, the actuator sub-assembly can be mounted to the base support member 106 (in this case the pelvic region) and the pivot device 140 can be fixed relative to the rotary support member 102 (or the upper leg support member).

Although many of the embodiments described herein locate the actuator sub-assembly inside the rotary support member, it is to be appreciated that either configuration can allow for powered rotation of the rotary support member relative to the base support member by the biomimetic mechanical joint. Furthermore, the base support member can comprise a rigid body section of the human-like robotic device, such as the torso, as well as the rotary support member of an adjacent joint.

Figures 3, 4:
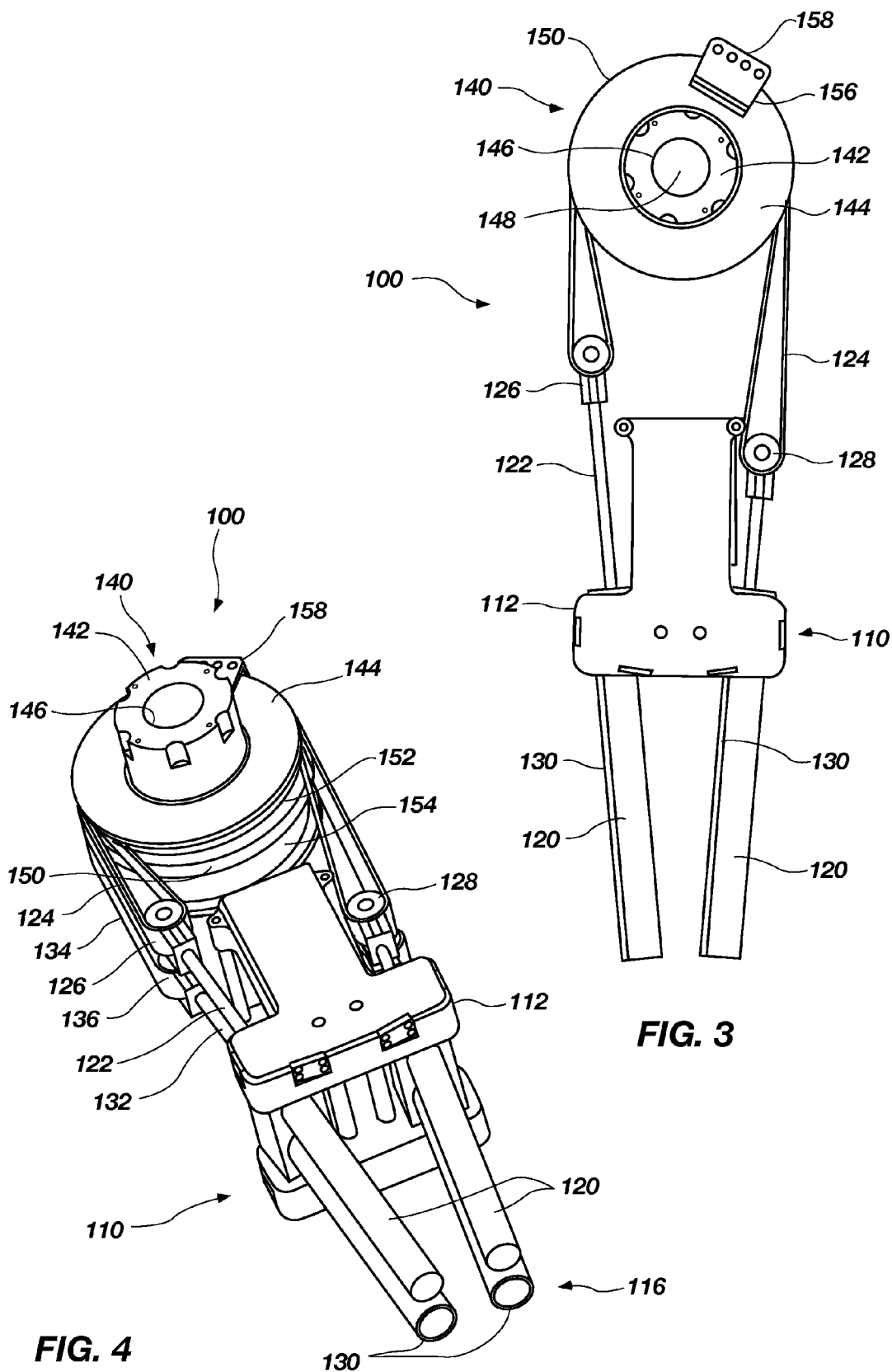
FIG. 3 illustrates a close-up side view of the biomimetic mechanical joint of FIG. 2.
FIG. 4 illustrates a close-up perspective view of the biomimetic mechanical joint of FIG. 2.

To better illustrate the configuration and operation of the fractional actuators, tendons, and pivot device, the biomimetic mechanical joint of FIG. 2 is shown in more detail in FIGS. 3 and 4 without the rigid outer shell. The two fractional actuators 116 included in the actuator sub-assembly 110 can be further comprised of two antagonistic actuator pairs 120, 130. Each antagonistic actuator pair can be considered a single fractional actuator, since each individual actuator in the antagonistic actuator pair is a linear, single-acting actuator that can only move the support member about the pivot device in one direction (e.g. one can only pull on a tendon attached to a pivot device, not push). The fractional actuators, however, can be configured for rotation in both directions. Therefore, for the exemplary biomimetic mechanical joint of FIGS. 2-4, the two single-acting actuators and tendon in one antagonistic actuator pair (120 or 130) can together be considered to be a single fractional actuator 116 for the purposes of the method of the present invention.

The two antagonistic actuator pairs can also be of different sizes, including a large actuator pair 130 and a small actuator pair 120. Moreover, each antagonistic actuator pair can have symmetric actuators, meaning that both single-acting actuators in the same pair are of similar size and configuration, and can generate equivalent forces in both directions. If the fractional actuators are hydraulic cylinders, one actuator pair can be provided with small diameter hydraulic cylinders that are sized for high-speed/low-load conditions. For a given flowrate of fluid from the control body 112, the small diameter actuator pair 120 will rotate the pulley faster than the large diameter pair, but with reduced force. For the same flowrate, the larger diameter actuator pair 130 will rotate the pulley at a slower rate, but with more force pulling on the tendon, since the force imparted by the actuator is directly proportional the surface area of the piston face.

The pivot device 140 can be comprised of a pulley having a disc portion 144 and an axle portion 142. The pulley can rotate about a pivot post 148 which fits inside a center hole 146 in the axle portion of the pulley. The disc portion 142 can have an outer circumferential surface 150 into which are formed a plurality of tendon grooves 152, 154, with one groove for each tendon 124, 134 of each antagonist actuator pair 120, 130. Also formed in the pulley's circumferential surface can be an attachment slot 156 that axially bisects the tendon grooves and provides a location for a tendon attachment block 158 to be mounted to the pulley. Situated within the pivot post 148 or the center hole 146 can be a rotating interface such as a bearing or a bushing (not shown), which allows the pulley and the pivot post to rotate relative to one another.

Each antagonistic actuator pair 120, 130 can have two symmetrically-sized actuators linked together over the pivot device 140 with a tendon 124, 134. Although the tendons may be provided in a variety of shapes sizes, each tendon in the embodiment 100 shown in FIGS. 2-4 can have a belt-shaped profile with a defined width and thickness, and can further be configured with dimensions that match the width and thickness of the corresponding tendon groove 152, 154. Each tendon can also be coupled at their midsection to the attachment block 158 connected to the pivot device, which fixes the tendons to the pivot device and prevents slippage of the tendons within the grooves.

The ends of each tendon 124, 134 can be attached with end connectors 126, 136 to the ends of the actuator pistons 122, 132 by any means available in the art. In the embodiment shown, for example, the tendons can be made sufficiently long so that the ends can be looped back and connected to the attachment block 158, and the end connectors configured with connector rods 128 that fit within the tendon loops and secure the tendons to the actuator pistons. The looped configuration can be advantageous by allowing for small movements of the tendons relative to the actuator pistons during operation as the tendons are alternately wrapped and unwrapped around the pulley, which movements can relieve stress and reduce wear, and further ensure that the load acting on the actuators 120, 130 is in pure tension.

The ends of the two tendons 124, 134 can be separately attached to their respective actuator pistons 122, 132 with the end connectors 126, 136 to allow relative movement between the two tendons in response to varying load conditions, e.g. a loaded tendon can stretch more than an unloaded tendon. For instance, if the large actuator pair 130 is active and the small actuator pair 120 is inactive or disengaged, the segment of the tendon 134 attached to the working large actuator can stretch slightly under load, while the segment of the tendon 124 for the adjacent small actuator can remain slack. Even though both tendons can be fixed to the pulley 144 with the attachment block 158, only the segment of the tendon 134 connected to the working, large actuator may pull on the pulley to rotate the pivot device 140. On the opposite side of the actuator sub-assembly 110, however, both the small and large inactive actuators can follow the movement of their respective tendons 124, 134 as they roll up onto the pulley 144 while the active working actuator rotates the support member about the pivot device.

In an alternative embodiment, the tendons 124, 134 can be linked together at the end connectors 126, 136 such as with a extra-long, common connector rod 128. And in another alternative embodiment, the two antagonistic actuator pairs can share a common end connector coupled to a single, double-wide tendon-belt.

The pulleys may be sized and configured to provide the optimal performance with respect to the actuators operable with them. In other words, providing different sized (e.g., different diameter) pulleys, pulleys with variable radii, or a combination of these, can contribute to the variables in creating the control logic used to operate the biomimetic mechanical joint. For example, the mechanical advantage provided by one or more variable radius pulleys may contribute to the analysis undertaken to determine the appropriate type and/or size of actuators made operable with the pulleys. In addition, the configuration of the pulley(s), the attachment arrangement of the tendons, etc. may also contribute to such analysis.

If either of the fractional actuators 120, 130 is selectively recruited at any particular moment in time to power the biomimetic mechanical joint 100, the actuator not recruited at that instant can be selectively disengaged or disconnected from the mechanical joint to prevent unnecessary drag on the active portion of the actuator system. This selective disengagement can include fluidic disengagement between the actuators and the pivot device, physical disconnection of the actuators from the pivot device, or electrical disconnection between a motor and a power supply, etc. Illustrated in FIG. 5 is a schematic diagram of an exemplary biomimetic mechanical joint 200, similar to the biomimetic mechanical joint 100, which can further demonstrate the fluidic disengagement of the non-active actuator from the biomimetic mechanical joint during single actuator operation.

Figure 5:
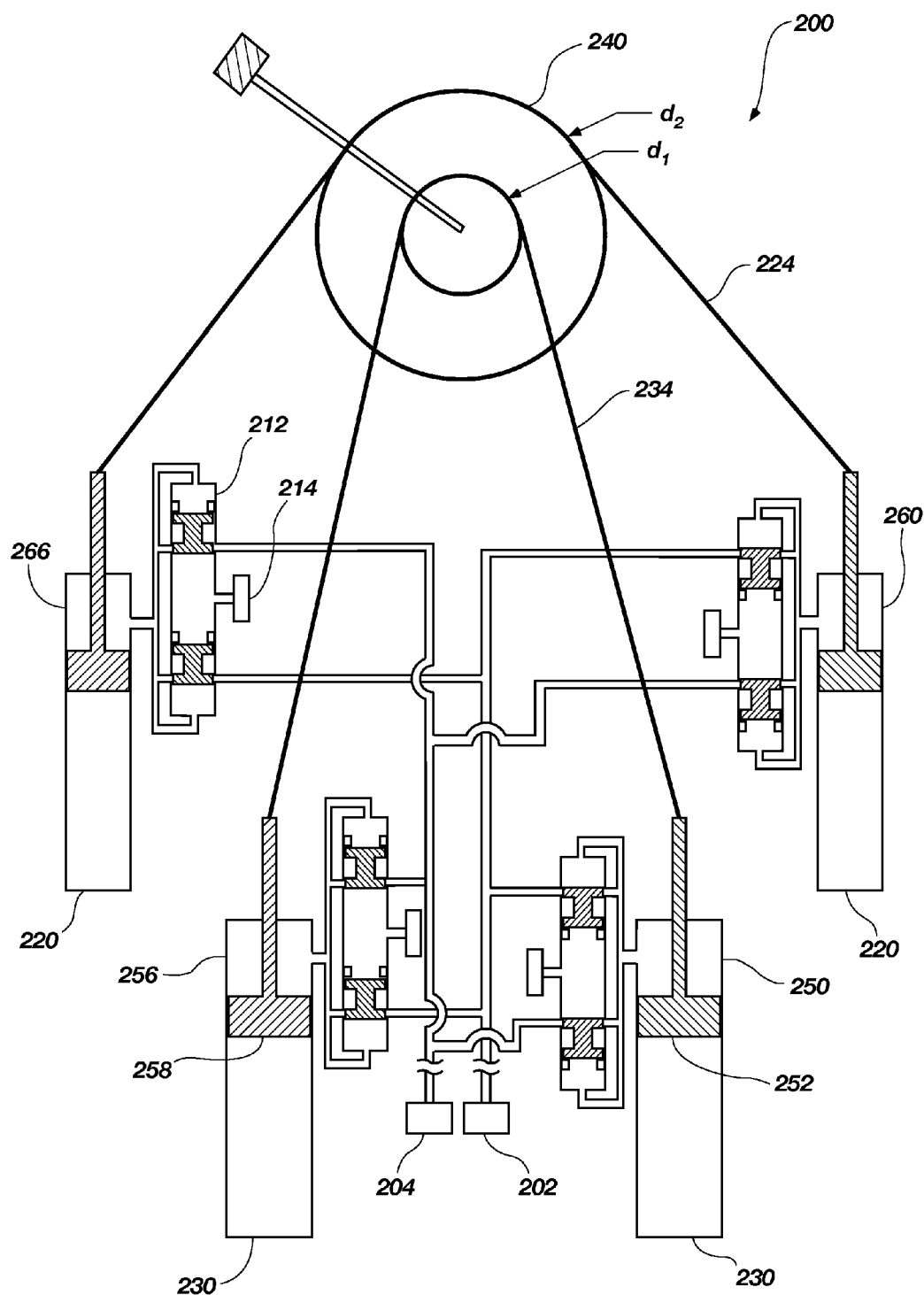
FIG. 5 illustrates a schematic diagram of another exemplary biomimetic mechanical joint with fractional actuators and operated in accordance with an exemplary embodiment of the present invention.

In the exemplary biomimetic mechanical joint 200 illustrated in FIG. 5, the pivot device 240 is acted upon by a small antagonistic actuator pair 220 and a large antagonistic actuator pair 230, both of which are connected to the pivot device with tendons 224, 234, respectively, each being operable with a different sized pulley, shown as pulleys having diameters $d_1$ and $d_2$. Each individual actuator in each antagonistic actuator pair can be a single-acting, linear hydraulic actuator, which can be connected at the head end of the hydraulic cylinder to a pressure control valve (PCV) 212 operable with a pilot valve 214. The PCVs and pilot valves can be configured so that the inactive antagonistic actuator pair operates in accordance with a "slosh" mode, which allows the hydraulic fluid contained in the inactive antagonistic actuator pair to shunt back and forth between the two single-acting hydraulic cylinders without consuming or performing work. In other words, the inactive fractional actuator can be configured for idle operation by selecting the PCVs and pilot valves for slosh mode, which can disengage the fractional actuator from the system so that it does not contribute as a drag or brake on the biomimetic mechanical joint.

The hydraulic system which can utilize two antagonistic actuator pairs, in conjunction with corresponding PCVs and pilot valves, to allow for active operation of one actuator pair and slosh mode operation of the other, is described in more detail in commonly-owned and co-pending U.S. patent application Ser. No. 12/074,261, filed Feb. 28, 2008, entitled "Fluid Control System Having Selective Recruitable Actuators;" and Ser. No. 12/074,260, filed Feb. 28, 2008, entitled, "Antagonistic Fluid Control System for Active and Passive Actuator Operation," which applications are incorporated by reference in their entirety herein.

With reference to the actuation system illustrated in FIG. 5, the selectively recruitable and disengagable actuators can be operated in single fractional actuator (e.g. antagonistic actuator pair) mode. For instance, high-pressure hydraulic fluid from a fluid source 202 can be directed into one actuator cylinder 250 of an active actuator pair (in this case, large fractional actuator pair 230), expanding the cylinder chamber and pushing the actuator piston 252 away from the head end of the cylinder to pull on the active tendon 234 and rotate the pivot device 240. The opposite end of the active tendon can be connected to the cylinder 256, which actuator piston 258 is pulled toward the head end of the cylinder 256, contracting the cylinder volume and discharging the hydraulic fluid contained within the cylinder to the low pressure return reservoir 204.

At the same time, the volume of the opposite actuator cylinder 266 in the inactive antagonistic actuator pair 220 is also contracting, but instead of the fluid discharging to the return reservoir, the fluid can be shunted to the inactive actuator cylinder 260 adjacent the first fractional actuator 250 in the active actuator pair, which allows the inactive actuator 260 to passively react and follow along with the first active actuator 250. This is advantageous, because if at some point in mid-stroke the torque demand on the joint is suddenly increased, the inactive actuator pair is already in position and filled with fluid, and instantly available to activate and contribute to pulling on the pulley device 240 and without having to move and take up slack in the tendon.

Figure 6:
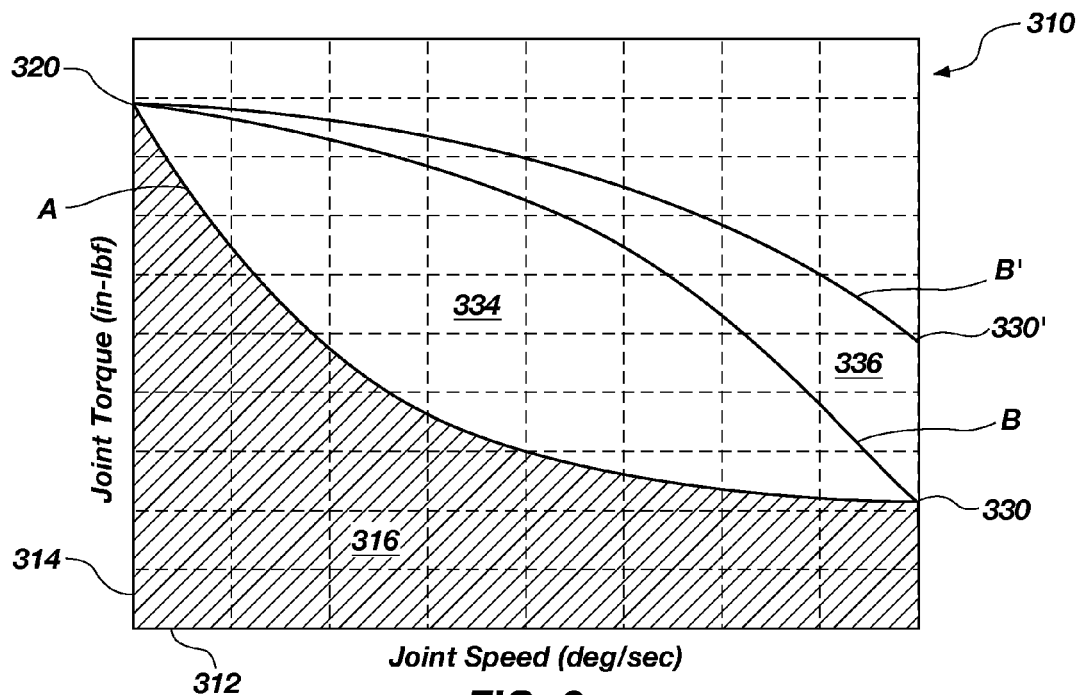
FIG. 6 is a plot illustrating representative demand and generated power curves characteristic of an actuated mechanical joint as known in the prior art.

Illustrated in FIG. 6 is a plot 310 of several speed-torque curves, or power curves, that can be used to model the power generated within or utilized by a mechanical joint of the prior art utilizing a single 100% actuator. The X-axis 312 of the plot can define the speed of the joint in rotating the limb or support member about the pivot device, in units of degrees/second. The Y-axis 314 of the plot can define the torque which can be either generated by the actuators or utilized by the joint in rotating the support member about the pivot device, in units of in-lbf. The first speed-torque curve A is an illustrative example of a demand power curve, which exemplifies the power that can be required by a mechanical joint across its operating range. The second speed-torque curve B is an illustrative example of a generated power curve, which exemplifies the power that can be generated by a single actuator-type system across the same operating range.

The general relationship between speed and torque is inversely proportional for both the demand power curve A and the generated power curve B, in that high torques can be generated or utilized at lower speeds, and high speeds can be generated or utilized with lower torques. Furthermore, the generated curve B must always be greater than or equal to the demand curve A, otherwise the mechanical joint would fail to function fully.

Specifically referring to the demand power (or speed-torque) curve A, the mechanical joint system can have two boundary conditions at either end of the curve. The left-most boundary condition 320 corresponds to the maximum torque that may be required of the mechanical joint. As can be appreciated by one having skill in the art, the biomimetic mechanical joint can have a maximum torque (e.g. low-speed/high-torque) boundary condition which corresponds to applying a maximum torque with very little motion. A physical example could be rotating the support member while lifting a heavy load, or climbing a staircase with all the weight momentarily carried by one leg. In order to rotate the same support member with more speed, however, the laws of physics dictate that the load on the mechanical joint be decreased, as demonstrated by following the demand power curve A to the right, towards the other end of the plot. The right-most boundary condition 330 corresponds to the maximum design rotational speed (e.g. high-speed/low-torque) of the support member about the pivot device. In the physical world, this is the fastest rotation that can be accomplished when the support member is moved solely against the influence of its own weight, or base gravity loading.

With the demand power curve A, the curve can be continuous and smooth, without any sudden breaks or steps, between the maximum torque boundary condition 320 and maximum speed boundary condition 330. Moreover, the demand power curve A required by the biomimetic mechanical joint can have a generally downwardly-bowed shape, which curve shape is typical of the torque demanded by a mechanical joint while moving through the operating speed range of the system. The region 316 bounded by the X-axis, Y-axis and the demand curve A can define the normal operating range of the biomimetic mechanical joint, with demand curve A defining the maximum torque demanded at any particular speed. Points below demand curve A also fall within the operating range, and can be reaching by throttling or otherwise reducing the power to the joint.

Also shown in plot 310 is the generated power (or speed-torque) curve B, which can illustrate the power provided by a single, 100% actuator system that has been configured to meet both the maximum design torque (or boundary condition) 320 and the maximum design speed (or boundary condition) 330 of the mechanical joint. The generated power curve B can be representative of both hydraulic and electrical actuator systems. In physical terms of a hydraulic system, the diameter of the cylinder's bore can be made large enough to generate a force sufficiently large to reach the maximum design torque 320, while at the same time, the associated servo-valve or control system can be given enough throughput capacity to quickly fill the cylinder and move the joint at the maximum design speed 330.

As can be seen in FIG. 6, the generated power curve B can have the same general left-to-right downward-sloping form as the demand power curve A. In contrast to the demand power curve A, however, the generated power curve B produced by the actuator system can have a generally upwardly-bowed shape, which is characteristic of many actuation systems using single, 100% actuators. The difference between the two curves, as identified by the region 334, illustrates the lost power, or inefficiency, that is inherent within a mechanical joint driven by a single, 100% actuator system.

When the single actuator is configured to meet both extreme boundary conditions of the joint, e.g. the maximum design torque 320 and the maximum design speed 330, excess power will be wasted during operation on the curve between the two end points, as indicated by the region 334 between curves A and B. In a hydraulic system, this lost power can be manifested as high pressure fluid that is throttled as it passes through the servo-valve controlling the actuator. In a motorized system, this lost power can be manifested as wasted electricity and excess heat that is generated as the motor operates at a less efficient voltage level.

Under optimum conditions the area 334 would be the only loss or inefficiency between the generated power curve B and the demand power curve A. However, in many circumstances it may not be possible for a single actuator to be configured to meet both boundary conditions 320 and 330. In such conditions the system will often be designed around the maximum torque boundary condition 320 and left oversized for the maximum speed boundary condition 330. This can have the affect of moving the optimum generated power curve B to an actual generated power curve position B', and the generated power at the high-speed/low-load boundary condition from the optimum capability 330 to an oversized capability 330'. This can result in additional wasted energy when the actuator is operated at higher speeds, as exemplified by region 336. In physical terms of the hydraulic actuation system example, the wasted energy can be embodied in the excess high-pressure hydraulic fluid that is required to move the large-diameter hydraulic piston under a little or no load.

Figure 7:
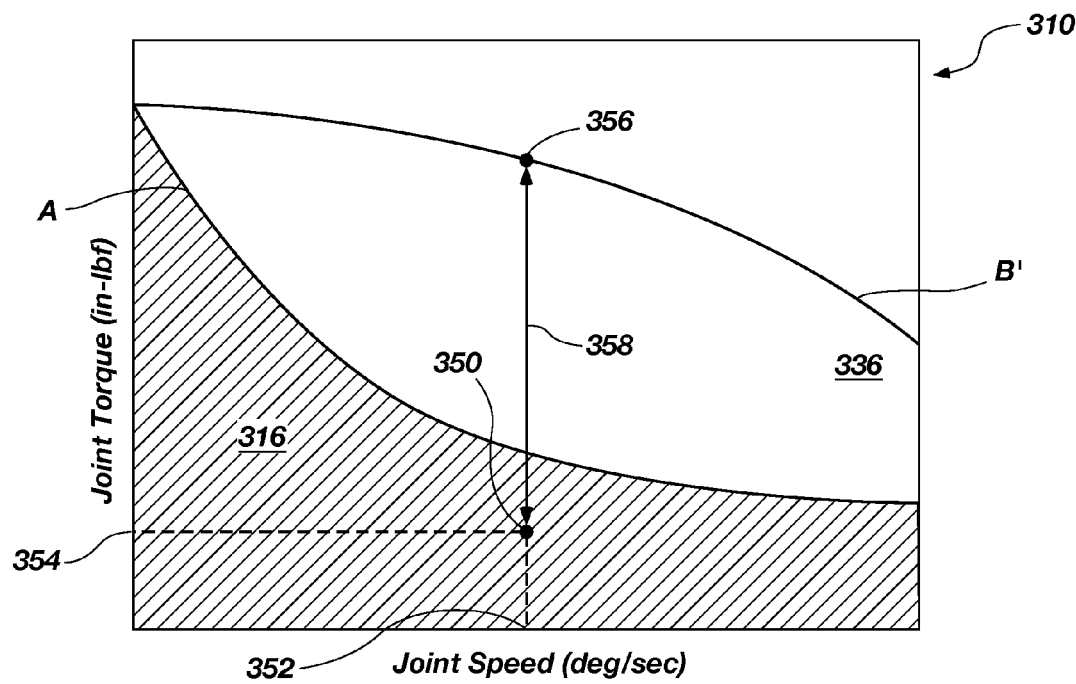
FIG. 7 is a plot illustrating representative operating characteristics of the prior art mechanical joint of FIG. 6.

This inefficiency is further illustrated in FIG. 7, which is a plot illustrating the representative operating characteristics of the single, 100% actuator prior art mechanical joint of FIG. 6. For example, it may be desirable or commanded by the operator of the robotic device that the mechanical joint perform at an operating point 350 included within the operating range 316 of the mechanical joint, to provide a specified level of torque 354 at a specified speed 352. To reach this operating point, the single 100% actuator is limited to a sole operating state 356 on its actual generated power curve B' that matches the desired speed of the joint. However, at this state the actuator will provide an excess of torque or power to the joint, which must be throttled through a throttle range 358 if the mechanical joint is to maintain the specified operating speed 352. In the physical terms of a hydraulic system, the pressure of the hydraulic fluid will be throttled by the actuator's inlet valve before entering the hydraulic cylinder, in order to maintain the desired balance of forces between the applied load and the torque provided by the mechanical joint.

It can be appreciated that even while the single 100% actuator of the prior art mechanical joint can operate at less-than-optimum speeds and torques, the throttle range 158 constitutes a significant waste of potential energy for just one movement of the mechanical joint. When multiplied over time, and by the plurality of mechanical joints that could be integrated into a single robotic device, this wasted energy can add up to a significant drain on a finite fuel resource.

Figure 8:
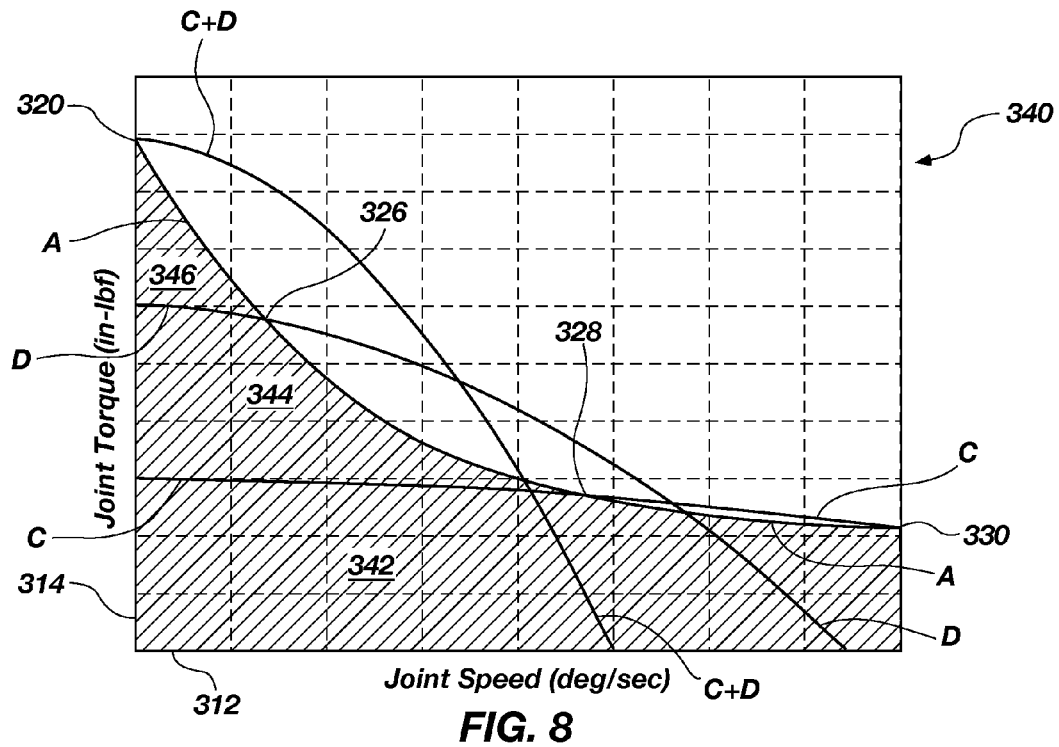
FIG. 8 is a plot illustrating representative demand and generated power curves characteristic of a biomimetic mechanical joint having fractional actuators.

In contrast, shown in FIG. 8 is a plot 340 illustrating the benefits gained from configuring a biomimetic mechanical joint with a plurality of fractional actuators. In an exemplary embodiment, instead of designing a single, 100% actuator to meet the boundary conditions 320, 330 of the joint with inefficient operation between boundary conditions, the single 100% actuator can be divided into two factional actuators, one of which provides generated power curve C and the other which provides generated power curve D. Operating in combination, the two fractional actuators together can provide the generated power curve C+D. Although each fractional actuator still has the upwardly-bowed shape characteristic of the single actuator, the angle of the curve and degree of curvature can be configured to provide a better approximation of the demand power curve A, both individually and in combination. In another aspect of the biomimetic mechanical joint, the single actuator can be divided into three or more fractional actuators.

The small fractional actuator providing the generated power curve C can be configured to meet the maximum speed (high-speed/low-torque) boundary condition 330 of the mechanical joint. By way of an illustrative example, generated power curve C could be produced by the small antagonistic actuator pair 120 described in FIGS. 2-4. The fractional actuator and its associated control system 112 could be sized (or speed rated) to provide enough high-pressure hydraulic fluid to the hydraulic cylinder to move the small actuator piston 122 at a speed sufficient to rotate the mass of the structural member 102, without any additional loading, about the pivot device 140 at a rotational velocity that equals the maximum speed boundary condition 330 (see FIG. 8). By using only the small antagonistic actuator pair 120 to rotate the structural member 102 under such conditions, only the minimum amount of high-pressure hydraulic fluid is used, resulting in less wastage in comparison to other cylinder configurations.

It can also be appreciated that the small actuator can be continuously throttled to provide a more efficient power source for all operating points falling below power curve C, or within region 342, even those at a slow speed.

The generated power curve D could be produced by the large antagonistic actuator pair 130 described in FIGS. 2-4. With its larger size hydraulic cylinders, the large fractional actuator can assume sole operation of the biomimetic mechanical joint 100 whenever the demand torque is greater than generated power curve C, but still less than the maximum required of the joint. Referring back to FIG. 8, generated power curve D can be the optimum actuator selection between operating points 326 and 328. The large fractional actuator can also be continuously throttled to provide a more efficient power source for all operating points between power curves C and D, or within region 344.

Both fractional actuators would not need to be recruited together unless the biomimetic mechanical joint encountered an operating point that demanded more torque than could be provided by the single large actuator, as would be the case for all operating points falling inside the region 346, located to the left of point 326 and between demand power curve A and generated power curve D. As this dual-actuator region only covers a small portion of the entire operating range of the mechanical joint, it can readily be seen that significant energy savings can be realized with a biomimetic mechanical joint having fractional actuators, as the actuation system could be operated with either the large or small fractional actuator in single-actuator operation over the majority of the operating range of the joint.

A method for sizing the fractional actuators to meet the projected speed and torque requirements of the biomimetic mechanical joint is described in commonly-owned and co-pending Patent Application No. PCT/US09/55440, filed Aug. 28, 2009, and entitled "Method Of Sizing Actuators For A Biomimetic Mechanical Joint", which application is incorporated by reference in its entirety herein.

A biomimetic mechanical joint driven by a plurality of continuously throttled fractional actuators can operate with two control degrees of freedom, e.g. the recruitment arrangement of the actuators and the throttle settings. In some conditions, this may provide the mechanical joint with the choice of more than one actuator recruitment arrangement and throttle setting, or powering configuration, for a particular operating state. As more than one actuator recruitment arrangement is available, the present invention contemplates a control logic that can be used to select one of the available actuator recruitment arrangements, which may optimize one of strength, speed, and even efficiency for a given operating condition.

Figure 9:
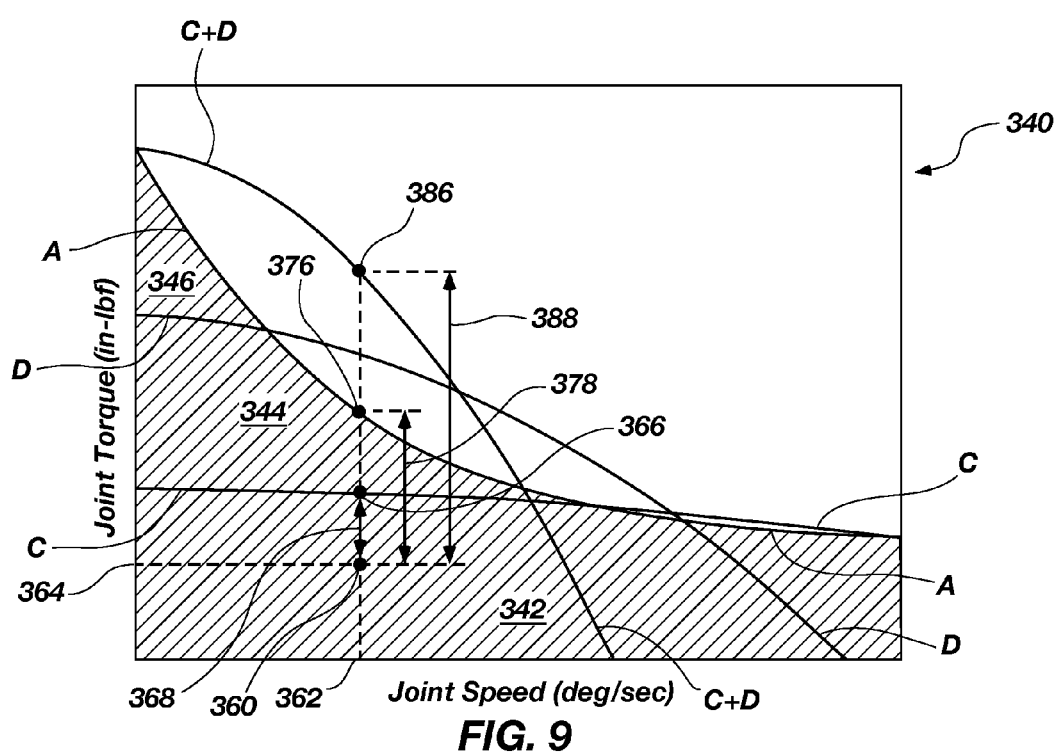
FIG. 9 is a plot illustrating representative operating characteristics of the biomimetic mechanical joint of FIG. 8.

Graphically illustrated in FIG. 9 in an example of an operating state with more than one potential powering configuration. As can be seen, operating point 360 corresponds with a load condition on the biomimetic mechanical joint 'demanding' a specified level of torque 364 at a specified rotational speed 362, which can fall within the operating envelopes of each fractional actuator when individually recruited (curve C, curve D), and the operating envelope of the combined actuators when recruited together (curve C+D). Therefore, the actuator system can meet the demands of operating point 360 by selectively recruiting the smaller actuator for operation at point 366 with a throttle range of 368, selectively recruiting the larger actuator for operation at point 376 with a throttle range of 378, or recruiting both actuators for operation at point 386 with a throttle range of 388. As the throttle range of 368 is significantly smaller than both throttle ranges 378 and 388, the smaller actuator alone can more efficiently drive the mechanical joint at operating point 360 than either the larger actuator alone or both actuators together. Thus, in one aspect of the present invention for operating in a high-efficiency mode, the criteria within the control logic for selecting between multiple powering configurations can be based on choosing the powering configuration with the smallest throttle setting.

It can be appreciated by one of skill in the art, however, that a powering configuration based on the smallest throttle setting may not simultaneously provide the most instantaneously available power for accelerating the mechanical joint to a new operating state in response, for instance, to a sudden increase in the externally-applied load. In the example described in FIG. 9, the most instantaneously available power for acceleration can be provided by the powering configuration 386, corresponding to the recruitment of both actuators for operation with the throttle range 388. Although the powering configuration 386 can be more wasteful than powering configuration 366, the mechanical joint can be more readily responsive to a sudden increase in demand torque and move the joint to a new operating state by simply reducing the degree of throttling. Thus, in one aspect of the present invention for operating in a high-acceleration mode, the criteria within the control logic for selecting between multiple powering configurations can be based on choosing the powering configuration with the largest throttle setting.

It can further be appreciated that a balance between high-efficiency and high-acceleration may at times be an advantageous operating mode, such as for general-purpose operation. Under these conditions, the criteria for selecting between multiple powering configurations within the control logic can be based on choosing the powering configuration with the throttle setting just greater than the lowest available throttle setting. In the illustrative example described in FIG. 9, this can correspond with powering configuration 376 and throttle range 378. Powering the biomimetic mechanical joint in the general purpose operating mode can provide the user with more readily available power for instantaneous acceleration when needed, but without the extreme waste of continuously engaging both fractional actuators.

Figure 10:
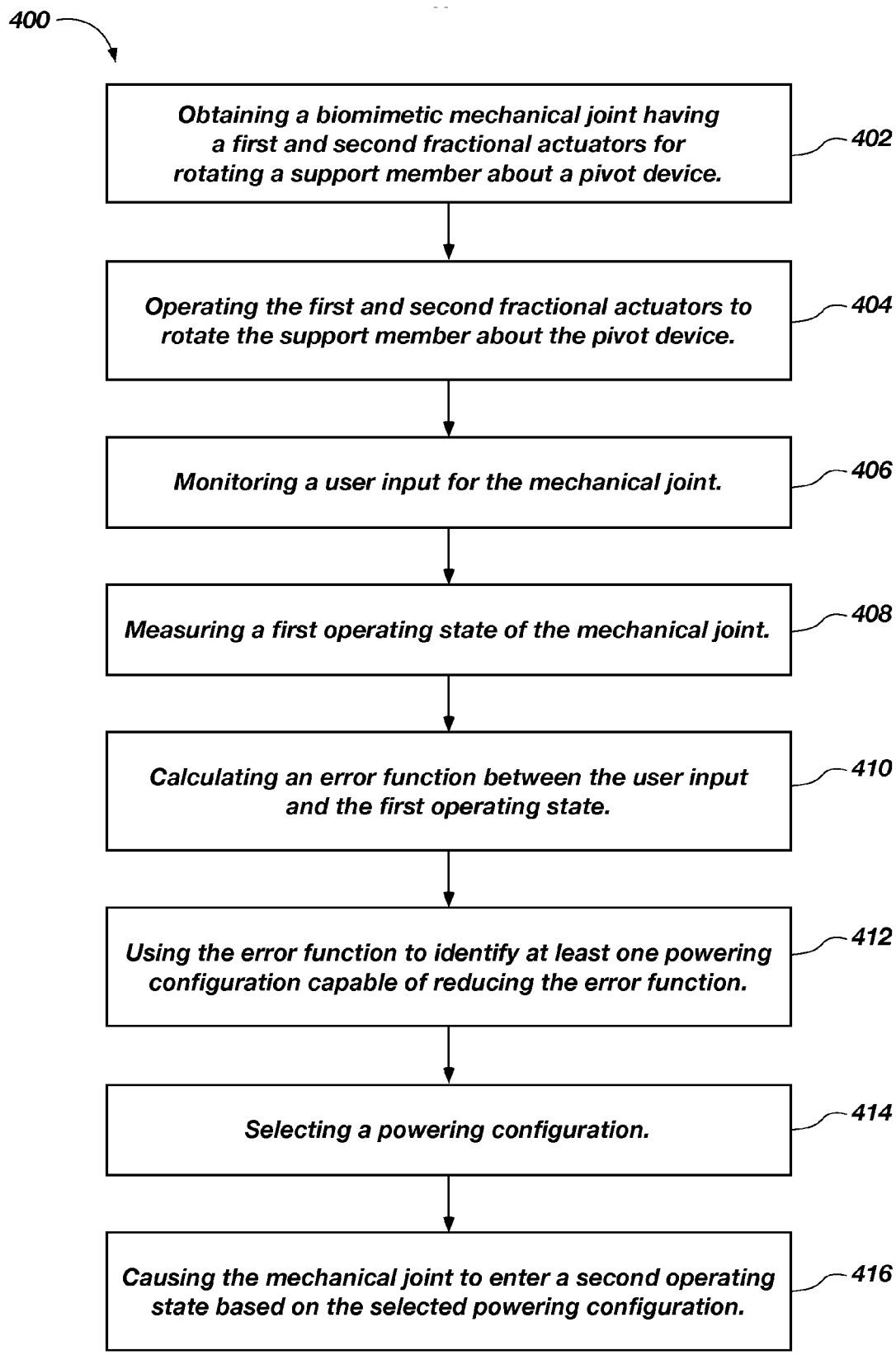
FIG. 10 is a flowchart depicting a method of operating a biomimetic mechanical joint with fractional actuators, in accordance with an exemplary embodiment of the present invention.

A method 400 for operating a biomimetic mechanical joint, in accordance with one exemplary embodiment of the present invention, is depicted in the flowchart of FIG. 10. This method describes one exemplary control logic platform and includes the step of obtaining 402 a biomimetic mechanical joint having first and a second fractional actuators that are configured for rotating a support member about a pivot device. Each of the first and second fractional actuators can be selectively recruited for and disengaged from driving the mechanical joint, and each can be continuously throttled when driving the mechanical joint. As described above, the ability to selectively recruit and throttle each of the first and second fractional actuators can result in an actuator sub-assembly having two control degrees of freedom, in which a single operating state of the mechanical joint may be reached with one or more actuator recruitment arrangements and throttling settings, or powering configurations.

The exemplary method also includes the step of operating 404 the first and second fractional actuators to rotate the support member about the pivot device. This will introduce the system to various operating states or conditions in which the control logic may selectively recruit different actuator arrangements to accommodate these.

The method further includes the step of monitoring 406 a user input for the mechanical joint. The user input can be a command torque received from the operator of the biomimetic system as forces sensed with load cells strategically placed on or otherwise supported about the mechanical limbs or frame of the biomimetic system, which may then be converted into command torques for each joint through a computation system. In one aspect of the present invention, the biomimetic robotic device can employ a plurality of force sensors attached to the robotic limbs or frame, which detect a baseline controlling interface force status relationship between the sensors and the extremities of the human operator. Based on the output force signal from the sensors, such as load cells, and the force and direction of gravity relative to the robotic frame, the computation system can calculate the command torque required to maintain the controlling force status relationship.

A contact displacement actuation system for measuring the force signal from the sensors and calculating the command torque required to maintain a controlling force status relationship between the sensors and the extremities of the human operator, is described in commonly-owned and co-pending U.S. patent application Ser. No. 11/879,448, filed Jul. 16, 2007, and entitled "Contact Displacement Actuator System", which application is incorporated by reference in its entirety herein.

The method 400 further includes the step of measuring 408 a first operating state of the biomimetic mechanical joint, which can be defined as the actual torque of the support member about the pivot device, or alternatively the actual torque and actual rotational speed of the support member about the pivot device. The first operating state can be referenced to an operating state of the mechanical joint which is at rest or in motion, and can be determined by any known system or method for measuring the torque and rotation speed of one structure relative to the other that is available in the art. Moreover, other operational parameters, such as the gravity vector acting on the joint, the recruitment arrangement of the actuators, the direction of rotation of the joint, the rotational position, displacement or direction of the joint, or the flow of hydraulic fluid into the joint's actuation system, can be included in the step of measuring the first operating state.

The step of measuring 408 a first operating state can also include the application of local and inter joint filters to separate out and remove any external motions or impulses generated by adjacent or nearby mechanical joints moving through their own operating regions. It is possible that shifting between actuator arrangements or altering the throttle settings in an adjacent mechanical joint may create momentary fluctuations and spikes in the measured torque or velocity in the biomimetic mechanical joint of interest, falsely prompting a shift into a different actuator arrangement. Local and inter joint filters can be used to filter out and remove these transient, external inputs. As can be appreciated, analog filters can be applied directly to the signals from the measurement devices, or digital filters can be applied later in the computational stages.

The method 400 still further includes the step of calculating 410 an error function between the user input and the first operating state. The error function can be defined as the difference between the command state and the operating state, and can be based on a variety of operational parameters of the mechanical joint. For instance, the error function can be calculated as the difference between the command torque and the actual torque of the mechanical joint, as measured in steps 406 and 408 above. In another aspect of the present invention the error function can be a power error function, which can be calculated as the difference between the desired joint power and the actual joint power through a computation that combines the command and actual torques as measured above with the actual rotational velocity of the joint in order to determine the actual and desired joint power.

In yet another aspect of the invention, the error function can be based on the difference between the command and actual flows of hydraulic fluid to the actuation system driving the mechanical joint. The error function can be based on the difference between as many actual and desired parameter values or operating states of the biomimetic mechanical joint as can be appreciated by one of skill in the art, and can further include tuning parameters, or proportional gain constants, to make the control system more or less responsive to operator input.

The step of calculating 410 an error function can further include the step of calculating an integral error function between the first operating state and a previous operating state or states. The integral error function can be combined with the error function in the calculation to accelerate the movement of the biomimetic joint towards the command input operating state and to reduce or eliminate accumulated errors in the computational process. In one aspect of the present invention the integral error function can be an integral torque error, but may be based on any measurable parameter of the biomimetic mechanical joint appreciated by one of skill in the art.

The method 400 of the present invention still further includes the step of using 412 the error function to identify at least one powering configuration for the first and second fractional actuators that is capable of minimizing or at least reducing the error function. As previously described (and illustrated in FIG. 9 above), a biomimetic mechanical joint having two or more continuously throttled, fractional actuators can have two control degrees of freedom, allowing for a single operating state of the mechanical joint to be reached with one or more actuator recruitment arrangements and throttling settings, or powering configurations.

In one aspect of the present invention, the one or more powering configurations that are capable of reducing the error function can be identified by comparing the error function with a set of pre-determined powering configurations (such as in a lookup repository (e.g., lookup table)) to identify the powering configurations capable of reducing the error function. The lookup repository can further include threshold values which allow for shifting between actuator recruitment arrangements. Providing a lookup table with shifting thresholds can simplify the process of identifying the powering configuration, thereby increasing the computational speed of the control system or reducing the speed requirements on the control system's processors.

In another aspect of the present invention, the step of using 412 the error function to identify available powering configurations can comprise inputting the error function (and integral error function, if applicable) into a continuous 'shifting logic' algorithm that calculates the one or more powering configurations capable of minimizing or at least reducing the error function. The shifting logic algorithm can include any processing method known in the art for applying the two control degrees of freedom, namely the arrangement or recruitment of the fractional actuators and their individual throttle settings, to identifying one or more powering configurations capable of reducing the error function.

The method 400 of the present invention further includes the step of selecting 414 a powering configuration from the identified one or more powering configurations that is capable of minimizing or at least reducing the error function. The step of selecting a powering configuration can be based on an operator-selectable operating mode, including but not limited to high-efficiency, high-acceleration, and general purpose operating mode or their equivalents, as pre-defined during the formation of the control system and in accordance with the intent of the operator. Moreover, the step of selecting a powering configuration can be based upon a particular joint operating parameter, including but not limited to actuator arrangement, throttle settings, current voltage, power flow, actuator pressure, flow of hydraulic fluid, etc.

By way of example, in one aspect of the present invention the high-efficiency mode can operate to select the powering configuration with the smallest throttle setting, while the general purpose mode can operate to select the powering configuration with the throttle setting just greater than the smallest throttle setting, and the high-acceleration mode can operate to select the powering configuration with the largest throttle setting. Other operating modes and joint operating parameters may be readily apparent and recognizable to one of skill in the art, which operating modes and joint operating parameters can be considered to fall within the scope of the present invention.

The step of selecting 414 a powering configuration from the identified one or more powering configurations can further include the application of a hysteresis or deadband control function to modify or delay the shifting of one actuator arrangement to another. As can be appreciated, the act of shifting between a first actuator arrangement to second actuator arrangement may not be completely smooth, and may create losses or instabilities in the measured operating parameter(s) which may otherwise prompt an immediate shift back into the first actuator arrangement. A hysteresis, or deadband, control can prevent a 'ping-pong'-like control response between actuator arrangements by delaying a shift between actuator arrangements until after the biomimetic mechanical joint has moved far enough into the new region of operation before shifting, to ensure that the joint can remain in the new actuator arrangement.

The method 400 of the present invention further includes the step of causing 416 the mechanical joint to enter a second operating state based on the selected powering configuration, which can comprise recruiting one or more of the first and second fractional actuators according to the actuator recruitment arrangement and throttle settings of the selected powering configuration. As the biomimetic mechanical joint moves into the second operating state, the process of monitoring the user input, measuring the new 'first' operating state, etc. can be continuously repeated, up to many times per second, so that the biomimetic robotic device smoothly follows the commands and movements of the operator.

Figure 11:
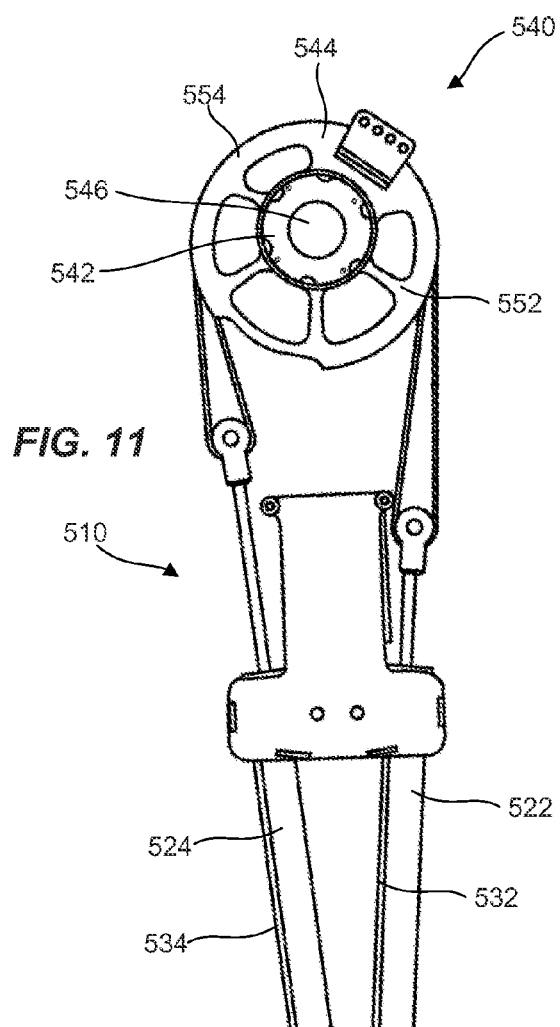
FIG. 11 illustrates a close-up side view of yet another biomimetic mechanical joint having fractional actuators and operated in accordance with an exemplary embodiment of the present invention.
Figure 12:
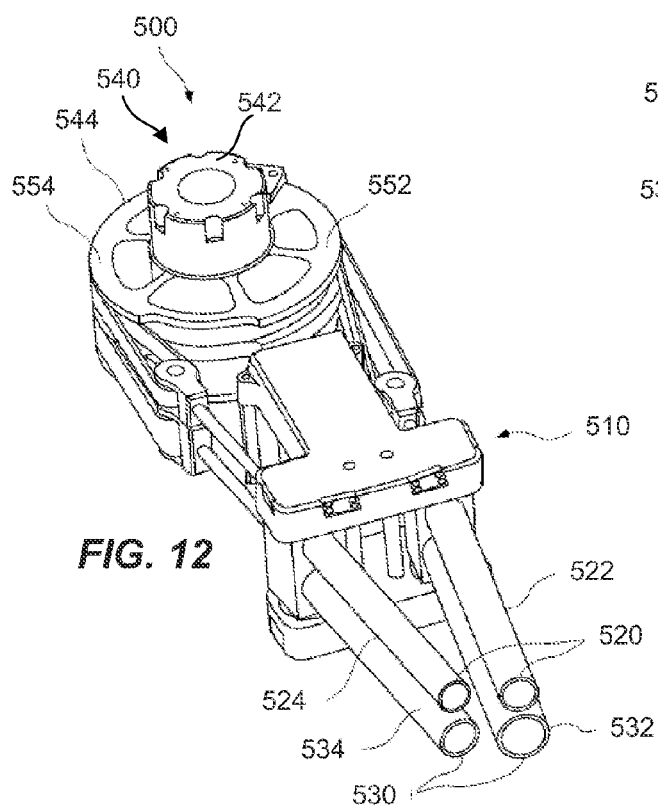
FIG. 12 illustrates a close-up perspective view of the biomimetic mechanical joint of FIG. 11.

Illustrated in FIGS. 11 and 12 is another exemplary biomimetic mechanical joint 500 which can also be operated in accordance with the method of the present invention. The biomimetic mechanical joint 500 is similar to the mechanical joint illustrated in FIGS. 2-5, in that the joint can be powered by two fractional antagonistic actuator pairs 520 and 530. However, the mechanical joint 500 is distinguishable from the previously-discussed joint in that the pivot device 540 can be a variable-radius or "VR" pulley 544 with an eccentric axle portion 542 and center hole 546. The mechanical joint 500 is further distinguishable in that each actuator in both antagonistic actuator pairs can be differentially sized from each of the other actuators in the actuator sub-assembly 510, in order to take further advantage of the leveraging aspects of the VR pulley, and thus better emulate the performance of the natural joint. Moreover, as discussed above, the different actuator pairs may each be operable with a differently sized and configured VR pulley to provide yet another selective variable for configuring and operating a biomimetic joint, and to further enhance the efficiency of the system. The control logic discussed herein may have factored in such differently sized and configured VR pulleys within a single joint in determining the operation of the various actuators operable with the pulleys.

By way of example, the small fractional antagonistic actuator pair 520 can have a large-radius actuator 522 which, when recruited, rotates the variable-radius pulley 544 using a large-radius portion of the 552 of the VR pulley, and a small-radius actuator 524 which, when recruited, rotates the pivot device using the small-radius portion of the 554 of the variable-radius pulley. In a similar fashion, the large, fractional antagonistic actuator pair 530 can have a large-radius actuator 532 and small-radius actuator 534 operating about the large-radius portion 552 and small-radius portion 554 of the variable-radius pulley, respectively.

The large-radius actuators 522, 532 can be differentially sized from their related small-radius actuators 524, 534 to take advantage of the mechanical advantage provided by the variable-radius pulley 544 and better emulate the performance of the natural joint. For instance, a natural joint may be capable of providing greater torque when moved in one direction verses the other (for instance, the quadriceps muscles can be significantly stronger than the hamstring muscles when rotating an upper leg member about the hip joint). When the variable-radius pulley 544 is assembled with an actuator sub-assembly 510 having differentially sized actuator pairs 522, 524 and 532, 534, the performance characteristics of the mechanical joint can be modified and extended, and may become dependent upon the direction of rotation of the mechanical joint. Consequently, the resulting biomimetic mechanical joint can better emulate the performance and efficiency of the natural joint.

The fractional actuators 520, 530 of the biomimetic mechanical joint 500 can be operated in accordance with the method of the present invention described in the flowchart of FIG. 10. The variable-radius pulley 544 and differentially-sized actuator pairs 520, 530 can allow for a smaller, lighter and more efficient actuation system that is better tailored to the operating demands of the mechanical joint 500, and with powering configurations that better conform to the demand curves of the joint. The method of operation for both the biomimetic mechanical joint 100 illustrated and described in FIGS. 2-4 and the biomimetic mechanical joint illustrated and described in FIGS. 11-12 can be substantially similar, with a distinguishing difference in that powering configurations can become dependent upon the direction of rotation of the support member about the pivot device. Regardless of the direction of rotation, however, the direction-specific powering configurations can be included in the lookup tables or incorporated into the "shifting logic" algorithm. Consequently, the steps of measuring a first operational state and calculating an error function, etc., can include added measurements of both the direction of rotation and rotational position or displacement of the mechanical joint, which parameters can be included throughout all the subsequent steps in the calculation processes.

The foregoing detailed description describes the invention with reference to specific exemplary embodiments. However, it will be appreciated that various modifications and changes can be made without departing from the scope of the present invention as set forth in the appended claims. The detailed description and accompanying drawings are to be regarded as merely illustrative, rather than as restrictive, and all such modifications or changes, if any, are intended to fall within the scope of the present invention as described and set forth herein.

More specifically, while illustrative exemplary embodiments of the invention have been described herein, the present invention is not limited to these embodiments, but includes any and all embodiments having modifications, omissions, combinations (e.g., of aspects across various embodiments), adaptations and/or alterations as would be appreciated by those in the art based on the foregoing detailed description. The limitations in the claims are to be interpreted broadly based on the language employed in the claims and not limited to examples described in the foregoing detailed description or during the prosecution of the application, which examples are to be construed as non-exclusive. For example, in the present disclosure, the term "preferably" is non-exclusive where it is intended to mean "preferably, but not limited to." Any steps recited in any method or process claims may be executed in any order and are not limited to the order presented in the claims. Means-plus-function or step-plus-function limitations will only be employed where for a specific claim limitation all of the following conditions are present in that limitation: a) "means for" or "step for" is expressly recited; and b) a corresponding function is expressly recited. The structure, material or acts that support the means-plus function are expressly recited in the description herein. Accordingly, the scope of the invention should be determined solely by the appended claims and their legal equivalents, rather than by the descriptions and examples given above.

What is claimed and desired to be secured by Letters Patent is:

1. A method of operating a biomimetic mechanical joint within a biomimetic system, the method comprising the steps of:
   obtaining a biomimetic mechanical joint having first and second fractional actuators configured for rotating a support member about a pivot device, wherein the first and second fractional actuators can be selectively recruited for and disengaged from driving the mechanical joint, and wherein each of the first and second fractional actuators can be continuously throttled when driving the mechanical joint;
   operating the first and second fractional actuators to rotate the support member about the pivot device;
   monitoring a user input for the mechanical joint;
   measuring a first operating state of the mechanical joint;
   calculating an error function between the user input and the first operating state;
   identifying, using the error function, at least one powering configuration for the first and second fractional actuators capable of reducing the error function;

selecting a powering configuration from the identified at least one powering configuration; and
causing the mechanical joint to enter a second operating state based on the selected powering configuration.

2. The method of claim 1, wherein the at least one powering configuration further comprises an actuator recruitment arrangement and a throttle setting for each of the first and second fractional actuators.

3. The method of claim 1, wherein said selecting a powering configuration from the identified at least one powering configuration further comprises selecting the powering configuration requiring a throttle setting selected from the largest throttle setting and the smallest throttle setting.

4. The method of claim 1, wherein said monitoring a user input for the mechanical joint further comprises monitoring a command torque derived from load cells supported about the biomimetic system.

5. The method of claim 1, wherein said measuring a first operating state of the mechanical joint further comprises measuring an actual torque and an actual rotating speed of the support member about the pivot device.

6. The method of claim 1, wherein said measuring a first operating state of the mechanical joint further comprises measuring a rotational position and direction of rotation of the support member about the pivot device.

7. The method of claim 1, further comprising implementing an inter joint filter to remove transient inputs from adjacent mechanical joints.

8. The method of claim 1, wherein said calculating an error function comprises calculating an error function selected from the group consisting of torque error, power error, joint hydraulic flow error, and any combination of these.

9. The method of claim 5, wherein said calculating an error function further comprises calculating an integral torque error function between the first operating state and a previous operating state.

10. The method of claim 1, wherein said identifying, using the error function, further comprises comparing the error function with a set of pre-determined powering configurations contained in a lookup repository to identify the at least one powering configuration capable of reducing the error function.

11. The method of claim 1, wherein said identifying, using the error function, further comprises inputting the error function into a continuous shifting logic algorithm to calculate the at least one powering configurations capable of reducing the error function.

12. The method of claim 1, wherein said selecting a powering configuration from the identified at least one powering configurations further comprises implementing a deadband control to delay changes to the actuator recruitment arrangement.

13. The method of claim 1, wherein said causing the mechanical joint to enter a second operating state further comprises recruiting one or more of the first and second fractional actuators according to the actuator recruitment arrangement and a throttle setting of the selected powering configuration.

14. A method of operating a biomimetic mechanical joint within a biomimetic system, the method comprising the steps of:
obtaining a biomimetic mechanical joint having first and second fractional actuators configured for rotating a support member about a pivot device, wherein the first and second fractional actuators can be selectively recruited for and disengaged from driving the mechanical joint, and wherein each of the first and second fractional actuators can be continuously throttled when driving the mechanical joint;
operating the first and second fractional actuators to rotate the support member about the pivot device;
monitoring an input command torque for the mechanical joint derived from load cells supported about a frame of the biomimetic system;
measuring a first operating state of the mechanical joint;
calculating an error function between the input command torque and the first operating state;
calculating an integral error function between the first operating state and a previous operating state;
identifying, using the error function and integral error function, at least one powering configuration capable of reducing the error function;
selecting from the identified at least one powering configurations; and
causing the mechanical joint to enter a second operating state based on the selected powering configuration.

15. The method of claim 14, wherein the at least one powering configuration further comprises an actuator recruitment arrangement and a throttle setting for each of the first and second fractional actuators.

16. The method of claim 14, wherein said selecting from the identified at least one powering configuration further comprises selecting the powering configuration requiring a throttle setting selected from the largest throttle setting and the smallest throttle setting.

17. The method of claim 14, wherein said calculating an integral error function further comprises calculating an integral torque error.

18. The method of claim 14, wherein said identifying at least one powering configuration further comprises utilizing an organizational lookup repository to identify the at least one powering configuration capable of reducing the error function.

19. The method of claim 14, wherein said identifying at least one powering configuration further comprises inputting the error function and integral error function into a continuous shifting logic algorithm to calculate the at least one powering configuration capable of reducing the error function.

20. The method of claim 14, wherein said causing the mechanical joint to enter a second operating state further comprises recruiting one or more of the first and second fractional actuators according to the actuator recruitment arrangement and a throttle setting of the selected powering configuration.

* * * * *